United States Patent
Fischer et al.

(10) Patent No.: US 9,890,113 B2
(45) Date of Patent: Feb. 13, 2018

(54) METHOD FOR CONTINUOUS PRODUCTION OF ADIPONITRILE

(71) Applicant: BASF SE, Ludwigshafen (DE)

(72) Inventors: Rolf-Hartmuth Fischer, Heidelberg (DE); Robert Baumann, Mannheim (DE); Veronika Wloka, Maxdorf (DE); Hermann Luyken, Heidelberg (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/510,949

(22) PCT Filed: Sep. 15, 2015

(86) PCT No.: PCT/EP2015/071031
§ 371 (c)(1),
(2) Date: Mar. 13, 2017

(87) PCT Pub. No.: WO2016/041930
PCT Pub. Date: Mar. 24, 2016

(65) Prior Publication Data
US 2017/0283369 A1    Oct. 5, 2017

(30) Foreign Application Priority Data

Sep. 16, 2014  (EP) ...................... 14184965

(51) Int. Cl.
*C07C 253/30*    (2006.01)
(52) U.S. Cl.
CPC .................................. *C07C 253/30* (2013.01)
(58) Field of Classification Search
CPC .................................................. C07C 253/30
See application file for complete search history.

(56) References Cited

U.S. PATENT DOCUMENTS

| | | | |
|---|---|---|---|
| 3,526,654 A | 9/1970 | Hildebrand | |
| 3,564,040 A | 2/1971 | Downing et al. | |
| 7,361,778 B2 * | 4/2008 | Bartsch | C07C 253/30 558/462 |
| 7,528,275 B2 | 5/2009 | Bartsch et al. | |
| 7,538,240 B2 | 5/2009 | Jungkamp et al. | |
| 7,612,224 B2 | 11/2009 | Scheidel et al. | |
| 7,816,551 B2 | 10/2010 | Jungkamp et al. | |
| 2008/0015379 A1 | 1/2008 | Garner et al. | |
| 2009/0182164 A1 | 7/2009 | Foo et al. | |

FOREIGN PATENT DOCUMENTS

| | | |
|---|---|---|
| WO | WO-2004094364 A1 | 11/2004 |
| WO | WO-2005073167 A1 | 8/2005 |
| WO | WO-2005073172 A1 | 8/2005 |
| WO | WO-2005073173 A1 | 8/2005 |
| WO | WO-2005073177 A1 | 8/2005 |

OTHER PUBLICATIONS

English Translation of International Preliminary Report On Patentability for PCT/EP2015/071031 dated Apr. 13, 2017.
International Preliminary Examination Report with Applicant amendments (in German) for PCT/EP2015/071031 dated Feb. 6, 2017.
International Search Report for PCT/EP2015/071031 dated Dec. 22, 2015.

* cited by examiner

*Primary Examiner* — Matthew Coughlin
(74) *Attorney, Agent, or Firm* — Drinker Biddle & Reath LLP

(57) ABSTRACT

A process for the continuous preparation of adiponitrile by hydrocyanation of 3-pentenenitrile is described, wherein
  a) 3-pentenenitrile is hydrocyanated to give a reaction output comprising adiponitrile,
  b) in a work-up 1, a mixture comprising cis-2-methyl-2-butenenitrile and cis-2-pentenenitrile is separated off as overhead product from the reaction output from the reactor R1 in a first distillation apparatus,
  c) the mixture comprising cis-2-methyl-2-butenenitrile and cis-2-pentenenitrile from step b) is continuously isomerized in the presence of aluminum oxide as catalyst in a reactor R2 to give a product mixture comprising 3-pentenenitrile,
  d) cis-2-methyl-2-butenenitrile is separated off as overhead product from the reaction output from the reactor R2 in a distillation apparatus in a work-up 2 and discharged.

20 Claims, 3 Drawing Sheets

METHOD FOR CONTINUOUS PRODUCTION OF ADIPONITRILE

CROSS-REFERENCE TO RELATED APPLICATIONS

Figure 1:
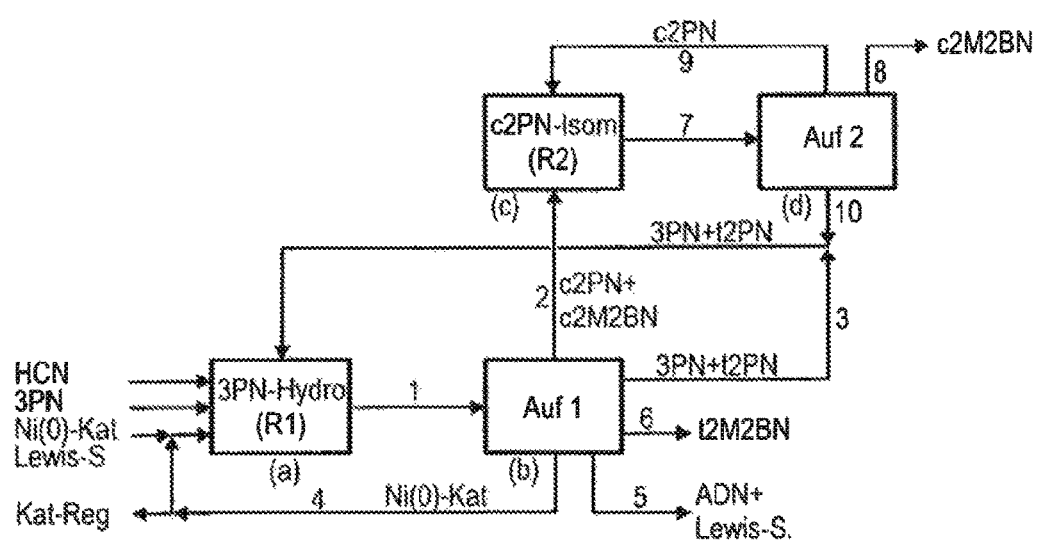

This application is a national stage application (under 35 U.S.C. § 371) of PCT/EP2015/071031, filed Sep. 15, 2015, which claims benefit of European Application No. 14184965.3, filed Sep. 16, 2014, both of which are incorporated herein by reference in their entirety.

The invention relates to processes for the continuous preparation of adiponitrile by hydrocyanation of 3-pentenenitrile, in which cis-2-pentenenitrile is isomerized to 3-pentenenitrile over a catalyst comprising aluminum oxide.

Adiponitrile is prepared industrially by three different processes. In detail, this is effected by i) reaction of adipic acid with ammonia, ii) by dimerization of acrylonitrile or iii) by hydrocyanation of butadiene by means of hydrocyanic acid.

Worldwide, adiponitrile is produced quite predominantly by hydrocyanation of butadiene.

In the first hydrocyanation step, butadiene is reacted with hydrocyanic acid in the presence of nickel(0)phosphorus ligand complexes to give mixtures comprising predominantly 3-pentene-nitrile and 2-methyl-3-butenenitrile. 3-Pentenenitrile and 2-methyl-3-butenenitrile are separated by distillation. 2-Methyl-3-butenenitrile is isomerized to 3-pentenenitrile.

In the second hydrocyanation step, 3-pentenenitrile is hydrocyanated by means of hydrocyanic acid in the presence of nickel(0)-phosphorus ligand complexes and additionally a Lewis acid to give adiponitrile.

The preparation of adiponitrile by hydrocyanation of 3-pentenenitrile is described, for example, in WO 2005/073173 or US 2009/182164 A1.

cis-2-Pentenenitrile and trans-2-pentenenitrile are formed in the hydrocyanation of 3-pentene-nitrile. The two isomers cannot be hydrocyanated by means of hydrocyanic acid to give adiponitrile in the presence of the nickel(0)-phosphorus ligand complexes or can be hydrocyanated only in the presence of specific Ni(0)-phosphorus ligand complexes (US 2008/15379 A1). Nevertheless, cis- and trans-2-pentenenitrile are potential products of value.

The table below shows that cis-2-pentenenitrile has a significantly lower boiling point than the remaining four linear pentenenitrile isomers and can therefore be separated off from the remaining linear pentenenitriles by distillation with a justifiable energy consumption.

$C_5$-Nitrile Boiling Points

| $C_5$-Nitriles | Boiling point (1013 mbar) |
| --- | --- |
| cis-2-Methyl-2-butenenitrile (=Z) | 120-123° C. |
| 2-Methyl-3-butenenitrile | 124° C. |
| cis-2-Pentenenitrile (cis-2-PN) | 127-128° C. |
| trans-2-Methyl-2-butenenitrile (=E) | 138° C. |
| trans-2-Pentenenitrile (trans-2-PN) | 143-145° C. |
| cis-3-Pentenenitrile (cis-3-PN) | 142-144° C. |
| trans-3-Pentenenitrile (trans-3-PN) | 142-146° C. |
| 4-Pentenenitrile (4-PN) | 140-147° C. |

Isomerization of cis-2-pentenenitrile in the presence of strongly basic compounds to give 3-pentenenitrile-comprising pentenenitrile mixtures is also known, see Prochazka et al., Collection of Czechoslovak Chemical Communications 1970, volume 35, pages 1224 to 1234. The isomerization was carried out at not more than 60° C. and atmospheric pressure using potassium tert-butoxide as base in tert-butanol as solvent. Obviously no Michael addition of the alcohol onto the acrylonitrile derivative cis-2-pentenenitrile ("3-ethylacrylonitrile") occurs at this temperature.

At 60° C., the thermodynamic equilibrium of the linear pentenenitriles corresponds to 39.6% of cis-2-pentenenitrile, 33.4% of trans-2-pentenenitrile, 8.5% of cis-3-pentenenitrile and 18.5% of trans-3-pentenenitrile, see table 6 in the abovementioned literature reference by Prochazka. Disadvantages for an industrial process are the low temperature which leads to long isomerization times, the use of a solvent and the necessity of recirculating the homogeneous catalyst.

The isomerization of 2-pentenenitrile to form trans-3-pentenenitrile in the presence of aluminum oxide as catalyst is known per se from WO 2004/094364. It is also stated that the cis-2-pentenenitrile used for the isomerization originates from the hydrocyanation of 3-pentenenitrile. According to the examples, the isomerization is carried out batchwise over aluminum oxide powder, which is not described in any more detail, at a temperature of from 126 to 144° C. It is merely indicated that the aluminum oxide should preferably have a BET surface area of from 70 to 350 $m^2/g$.

The four batchwise examples according to the invention were carried out at from 126 to 144° C. (table in WO 2004/094364). They show that the rate of isomerization to establishment of the isomerization equilibrium increases with increasing BET surface area of the $Al_2O_3$. However, oligomer formation also increases in the same direction. It is 0.17% at a BET surface area of 106 $m^2/g$, 0.84% at a BET surface area of 250 $m^2/g$ and 1.4% at a BET surface area of 349 $m^2/g$.

Comparative example 1 shows, on the other hand, that a BET surface area of 31.5 $m^2/g$ does not lead to full establishment of the equilibrium within 7 hours at 126-144° C. Only 3.7% of trans-3-+cis-3-pentenenitrile is formed.

Information on the continuous isomerization of cis-2-pentenenitrile in the liquid phase is not given in WO 2004/094364 A1.

The isomerization of cis-2-pentenenitrile to 3-pentenenitrile in a reactive distillation is described in WO 2005/073177, Extrudates composed of $Al_2O_3$ are used as catalyst. The temperature at the bottom is 149° C. according to the example. The $Al_2O_3$ catalyst is used in extrudate form. It is otherwise not described in more detail.

U.S. Pat. No. 3,526,654 discloses the isomerization of cis-2-pentenenitrile to 3-pentenenitrile in the presence of $Al_2O_3$ (2 examples), silica gel (2 examples) or sodium-calcium silicate (one example) in the liquid or gas phase at temperatures of from 25 to 500° C. over suspended or fixed-bed catalysts:

In example 1, the isomerization of cis-2-pentenenitrile is carried out continuously at 200° C. in the gas phase in the presence of Alcoa F—1 $Al_2O_3$ and nickel shaped bodies. The experiment was operated for only four hours. After this reaction time, the pentenenitrile isomer mixture comprised 43.3% of cis-2-pentenenitrile, 34.9% of trans-2-pentenenitrile, 5.9% of cis-3-pentenenitrile and 17.6% of trans-3-pentenenitrile.

A disadvantage of the gas-phase isomerization is that low catalyst operating lives have to be expected. When using cis-2-pentenenitrile, an acrylonitrile derivative, oligomer and/or polymer formation associated with deactivation of the catalyst has to be expected at 200° C.

In example 3, the cis-2-pentenenitrile isomerization is carried out batchwise at room temperature in the liquid phase in the presence of eta-Al$_2$O$_3$. After six months, the cis-2-pentenenitrile conversion is 40%. The pentenenitrile isomer mixture comprises 59.1% of cis-2-pentenenitrile, 24.1% of trans-2-pentenenitrile, 1.4% of cis-3-pentenenitrile and 15.4% of trans-3-pentenenitrile.

A reaction time of six months is uneconomical for an industrial process. A person skilled in the art has to conclude from the long reaction time that the reaction temperature should not be increased when working in the liquid phase.

Production plants for preparing adiponitrile (ADN) by hydrocyanation of butadiene and subsequently of 3-pentenenitrile have production capacities of 100 000 metric tons per annum and more. Continuous processes are therefore preferred for preparing such amounts of ADN.

It is therefore an object of the present invention to carry out the process step of isomerization of cis-2-pentenenitrile continuously and integrate this process for continuous isomerization into a continuous process for preparing adiponitrile from butadiene, hydrocyanic acid and hydrogen, without troublesome secondary components accumulating.

Preferably or as an alternative, the continuous isomerization should be realized using very few apparatuses and the work-up of the reaction products should particularly preferably be integrated in terms of apparatus.

A requirement is a long catalyst operating life, i.e. no significant deactivation of the isomerization catalyst should occur, and, furthermore, no troublesome coating of the catalyst or of parts of the apparatus by oligomers and/or polymers should occur. The isomerization should give a high product yield and space-time yield of hydrocyanatable intermediates and very small amounts of oligomers and polymers. Accumulation of the by-products cis- and trans-2-methyl-2-butenenitrile should be prevented.

The object is achieved according to the invention by a process, schematically shown in FIG. 1, for the continuous preparation of adiponitrile by hydrocyanation of 3-pentenenitrile, wherein a) 3-pentenenitrile or a mixture comprising 3-pentenenitrile is hydrocyanated by means of hydrocyanic acid in the presence of at least one nickel(0) complex as catalyst, free ligand, and at least one Lewis acid in a reactor R1 to give a reaction output comprising adiponitrile, 2-methylglutaronitrile, the nickel(0) complex, free ligand, Lewis acid, catalyst degradation products, unreacted 3-pentenenitrile and, as secondary components, cis- and trans-2-methyl-2-butenenitrile and also cis- and trans-2-pentenenitrile, b) in a work-up 1, a mixture comprising cis-2-methyl-2-butenenitrile and cis-2-pentenenitrile is separated off as overhead product, a mixture comprising adiponitrile, nickel(0) complex, free ligand, at least one Lewis acid and catalyst degradation products is separated off as bottom product and a mixture comprising trans-2-methyl-2-butenenitrile, trans-2-pentenenitrile and 3-pentenenitrile is separated off at a side offtake from the reaction output from the reactor R1 in a first distillation apparatus, the side offtake product is fractionated in a second distillation apparatus in such a way that trans-2-methyl-2-butenenitrile is separated off as overhead product and discharged and 3-pentenenitrile and trans-2-pentenenitrile are obtained as bottom product and recirculated to the 3-pentenenitrile hydrocyanation in step a), c) the mixture comprising cis-2-methyl-2-butenenitrile and cis-2-pentenenitrile from step b) is continuously isomerized in the presence of aluminum oxide as catalyst in a reactor R2 to give a product mixture comprising 3-pentenenitrile, where the isomerization is carried out at temperatures of from 120 to 220° C. and pressures of from 1 to 15 bar in the liquid phase and the aluminum oxide has a BET surface area of from 50 to 450 m$^2$/g and a pH of from 4 to 10.5, d) in a work-up 2 in a distillation apparatus, cis-2-methyl-2-butenenitrile is separated off as overhead product from the reaction output from the reactor R2 and discharged, unreacted cis-2-pentenenitrile is separated off from a side offtake and recirculated to the reactor R2 in step c) and the 3-pentenenitrile-comprising bottom product is recirculated to the 3-pentenenitrile hydrocyanation in step a).

The object is additionally achieved by a process for the continuous preparation of adiponitrile by hydrocyanation of 3-pentenenitrile, wherein a) 3-pentenenitrile or a mixture comprising 3-pentenenitrile is hydrocyanated by means of hydrocyanic acid in the presence of at least one nickel(0) complex as catalyst, free ligand, and at least one Lewis acid in a reactor R1 to give a reaction output comprising adiponitrile, 2-methylglutaronitrile, the nickel(0) complex, free ligand, Lewis acid, catalyst degradation products, unreacted 3-pentenenitrile and, as secondary components, cis- and trans-2-methyl-2-butenenitrile and also cis- and trans-2-pentenenitrile, b) in a work-up 1, only cis-2-methyl-2-butenenitrile is separated off as overhead product and all remaining compounds are separated off as bottom product from the reaction output from the reactor R1 in a first distillation apparatus and the bottom product from the first distillation apparatus is fractionated in a second distillation apparatus in such a way that cis-2-pentenenitrile is obtained as overhead product, 3-pentenenitrile, trans-2-pentenenitrile and trans-2-methyl-2-butenenitrile are obtained via a side offtake and crude adiponitrile, nickel(0) complex, free ligand, the at least one Lewis acid and catalyst degradation products are obtained as bottom product and the side offtake product from the second distillation apparatus is distilled in a third distillation apparatus in such a way that trans-2-methyl-2-butenenitrile is discharged as overhead product and a mixture comprising trans-2-pentenenitrile and 3-pentenenitrile is separated off as bottom product and recirculated to the 3-pentenenitrile hydrocyanation in step a), c) the cis-2-pentenenitrile from step b) is continuously isomerized in the presence of aluminum oxide as catalyst in a reactor R2 to give a 3-pentenenitrile-comprising product mixture, where the isomerization is carried out at temperatures of from 120 to 220° C. and pressures of from 1 to 15 bar in the liquid phase and the aluminum oxide has a BET surface area of from 50 to 450 m$^2$/g and a pH of from 4 to 10.5, d) unreacted cis-2-pentenenitrile is separated off as overhead product from the reaction output from the reactor R2 in a work-up 2 in a distillation apparatus and recirculated to the reactor R2 in step c) and the 3-pentenenitrile-comprising bottom product is recirculated to the 3-pentenenitrile hydrocyanation in step a).

The object is also achieved by a process for the continuous preparation of adiponitrile by hydrocyanation of 3-pentenenitrile, wherein a) 3-pentenenitrile or a mixture comprising 3-pentenenitrile is hydrocyanated by means of hydrocyanic acid in the presence of at least one nickel(0) complex as catalyst, free ligand, and at least one Lewis acid in a reactor R1 to give a reaction output comprising adiponitrile, 2-methylglutaronitrile, the nickel(0) complex, free ligand, Lewis acid, catalyst degradation products, unreacted 3-pentenenitrile and, as secondary components, cis- and trans-2-methyl-2-butenenitrile and also cis- and trans-2-pentenenitrile, b) in a work-up 1, a mixture comprising cis-2-methyl-2-butenenitrile and cis-2-pentenenitrile is separated off as overhead product, a mixture comprising adiponitrile, nickel(0) complex, free ligand, at least one Lewis acid and catalyst degradation products is separated off as bottom product and a mixture comprising trans-2-methyl-2-butenenitrile, trans-2-pentenenitrile and 3-pentenenitrile is separated off at a side offtake from the reaction output from the reactor R1 in a first distillation apparatus, and the side offtake product is fractionated in a second distillation apparatus in such a way that trans-2-methyl-2-butenenitrile is separated off as overhead product and discharged and 3-pentenenitrile and trans-2-pentenenitrile are obtained as bottom product and recirculated to the 3-pentenenitrile hydrocyanation in step a), c) the mixture comprising cis-2-methyl-2-butenenitrile and cis-2-pentenenitrile from step b) is continuously isomerized in the presence of aluminum oxide as catalyst in a reaction zone in a reactive distillation column R2 to give a 3-pentenenitrile-comprising product mixture, where the isomerization is carried out at temperatures of from 120 to 220° C. and pressures of from 1 to 15 bar in the liquid phase and the aluminum oxide has a BET surface area of from 50 to 450 $m^2/g$ and a pH of from 4 to 10.5, and cis-2-methyl-2-butenenitrile is separated off as overhead product and discharged, unreacted cis-2-pentenenitrile is separated off from a side offtake and recirculated to the reactor R2 in step c) and the 3-pentenenitrile-comprising bottom product is recirculated to the 3-pentenenitrile hydrocyanation in step a).

Furthermore, the object is achieved by a process for the continuous preparation of adiponitrile by hydrocyanation of 3-pentenenitrile, wherein a) 3-pentenenitrile or a mixture comprising 3-pentenenitrile is hydrocyanated by means of hydrocyanic acid in the presence of at least one nickel(0) complex as catalyst, free ligand, and at least one Lewis acid in a reactor R1 to give a reaction output comprising adiponitrile, 2-methylglutaronitrile, the nickel(0) complex, free ligand, Lewis acid, catalyst degradation products, unreacted 3-pentenenitrile and, as secondary components, cis- and trans-2-methyl-2-butenenitrile and also cis- and trans-2-pentenenitrile, b) in a work-up 1, only cis-2-methyl-2-butenenitrile is separated off as overhead product and all remaining compounds are separated off as bottom product from the reaction output from the reactor R1 in a first distillation apparatus and the bottom product from the first distillation apparatus is fractionated in a second distillation apparatus in such a way that cis-2-pentenenitrile is obtained as overhead product, 3-pentenenitrile, trans-2-pentenenitrile and trans-2-methyl-2-butenenitrile are obtained via a side offtake and crude adiponitrile, nickel(0) complex, free ligand, the at least one Lewis acid and catalyst degradation products are obtained as bottom product and the side offtake product from the second distillation apparatus is distilled in a third distillation apparatus in such a way that trans-2-methyl-2-butenenitrile is discharged as overhead product and a mixture comprising trans-2-pentenenitrile and 3-pentenenitrile is separated off as bottom product and recirculated to the 3-pentenenitrile hydrocyanation in step a), c) cis-2-pentenenitrile from step b) is continuously isomerized in the presence of aluminum oxide as catalyst in a reaction zone in a reactive distillation column R2 to give a 3-pentenenitrile-comprising product mixture, where the isomerization is carried out at temperatures of from 120 to 220° C. and pressures of from 1 to 15 bar in the liquid phase and the aluminum oxide has a BET surface area of from 50 to 450 $m^2/g$ and a pH of from 4 to 10.5, and unreacted cis-2-pentenenitrile is separated off as overhead product and recirculated to the reactor R2 in step c) and the 3-pentenenitrile-comprising bottom product is recirculated to the 3-pentenenitrile hydrocyanation in step a).

In an embodiment of the invention, an overhead product comprising cis-2-methyl-2-butenenitrile and cis-3-pentenenitrile is discharged in the work-up 1 in the first distillation apparatus and transferred to the subsequent isomerization. As an alternative, only cis-2-pentenenitrile can be discharged as overhead product in the first distillation apparatus and transferred to the isomerization.

A BRIEF DESCRIPTION OF THE FIGURES

FIG. 1 schematically illustrates an embodimemt of the continuous process of the invention for preparing adiponitrile from 3-pentenenitrile and hydrocyanic acid in the presence of nickel(0)-phosphorus ligand complexes as catalysts including the isomerization of cis-2-pentenenitrile to 3-pentenenitrile.

Figure 2:
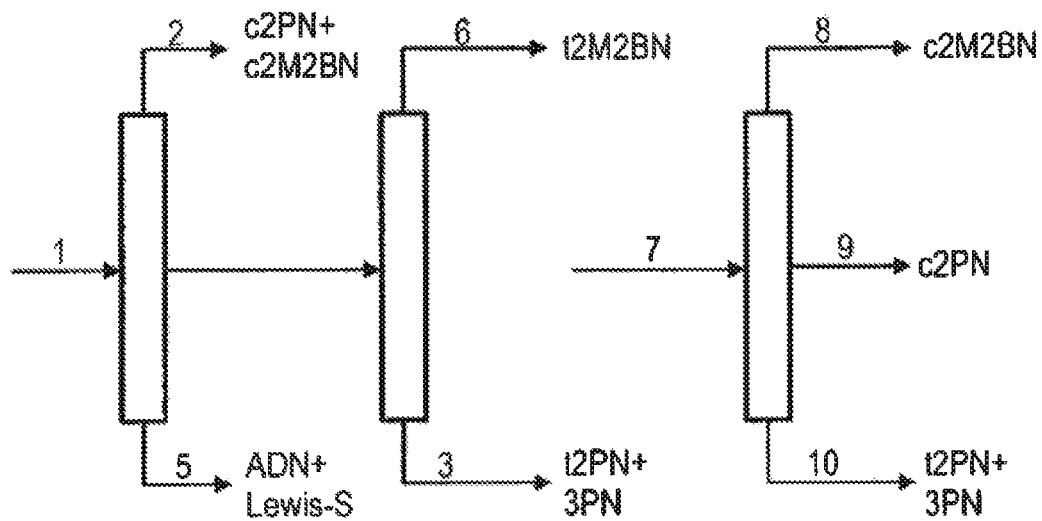

FIG. 2 schematically shows the work-ups 1 and 2.

Figure 3:
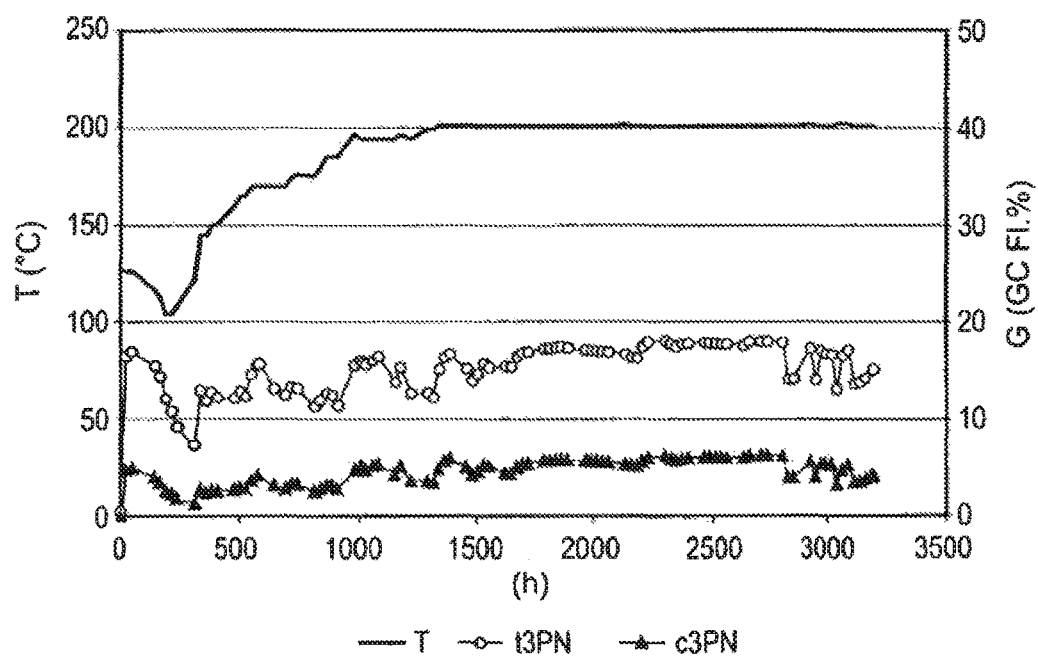

FIG. 3 shows the amounts (Content in percent by area in the gas chromatogram) of cis- and trans-3-pentenenitrile (PN) formed as a function of temperature (T) and reaction time (L).

In addition, it is possible to combine the isomerization in step c) with the work-up 2 in both embodiments of the process of the invention. Here, the isomerization is carried out in a reactive distillation column which typically comprises a bottom zone, a reaction zone and a top zone and can produce not only bottom and overhead discharge streams but can also have a further offtake. For an in-principle description of the reactive distillation and suitable apparatuses, reference is made to WO 2005/073177.

The process is carried out continuously. This means that each of the process steps indicated is carried out continuously, in contrast to a discontinuous or batch process. The configuration of the process steps corresponding to the continuous mode of operation is known to a person skilled in the art. Based on the overall process, the starting materials are introduced continuously into the process sequence and the process products are discharged continuously from the process sequence, so that the overall process can be operated continuously without interruption over a relatively long period of time. Interruptions to the course of the process can result only from excessively great catalyst deactivation, when the catalyst should or has to be replaced or regenerated. However, continuous discharge, regeneration or renewal of the catalyst can also be carried out.

It is in this sense that the term "continuous preparation" as employed in the claims should be understood.

According to the claims, products are separated off in the work-ups 1 and 2 and partly recirculated to other process steps.

Both the separation and the recirculation can in each case be in full or in part. This means that, according to the invention, partial recirculation of the respective streams to other process steps should also be encompassed, as should the only partial removal of individual components in the work-up.

The separation and recirculation are preferably carried out essentially in full or in full.

Furthermore, it is indicated that the reaction outputs or distillation outputs comprise particular components. It is also possible and preferred according to the invention for these mixtures to consist essentially or completely of the components indicated and thus comprise no significant amounts of further chemical compounds or no further chemical compounds.

The term "comprising" or "comprise" used according to the invention can thus preferably also mean "consisting essentially of" or "consists essentially of" or "consist" or "consists of".

For the purposes of the present patent application, the term 3-pentenenitrile refers to mixtures of the hydrocyanatable pentenenitrile isomers trans-3-pentenenitrile, cis-3-pentenenitrile and 4-pentenenitrile. The above table shows that all three isomers boil in the range from 140 to 147° C. at atmospheric pressure.

The mode of operation according to the invention allows the entire process and in particular the isomerization to be operated continuously over a long period of time. Even in the case of continuous isomerization in step b) at the preferred temperature of from 150 to 220° C., no troublesome oligomer formation which would deactivate the catalyst is observed.

It was to be expected that oligomer formation of 1.4% at from 126 to 144° C. in the batchwise experiment would lead to shortening of the catalyst operating life in continuous operation (from 150 to 220° C.) and to appreciable decreases in yield.

The individual process steps are explained in detail below.

The present invention provides a continuous process for preparing adiponitrile by hydrocyanation of 3-pentenenitrile by means of hydrocyanic acid in the presence of nickel(0)-phosphorus ligand complexes which preferably comprise bidentate or polydentate, in particular bidentate, phosphines, phosphonites, phosphinites or phosphites as ligands. Particular preference is given to bidentate phosphites. The isomerization of the by-product cis-2-pentenenitrile to 3-pentenenitrile and recirculation thereof is integrated into this hydrocyanation process:

The hydrocyanation of 3-pentenenitrile forms not only the target product adiponitrile but also branched dinitriles such as 2-methylglutaronitrile, the unhydrocyanatable pentenenitrile cis- and trans-2-pentenenitrile and the methylbutenenitriles cis- and trans-2-methyl-2-butenenitrile. In the work-up 1, crude adiponitrile and Lewis acid are discharged. Nickel (0) catalyst is separated off by extraction and, optionally after regeneration, recirculated to the 3-pentenenitrile hydrocyanation.

cis-2-Pentenenitrile can be separated off together with cis-2-methyl-2-butenenitrile from the remaining linear pentenenitriles trans-2-pentenenitrile, unreacted cis- and trans-3-pentenenitrile and 4-pentenenitrile by distillation and continuously isomerized to 3-pentenenitrile-comprising isomer mixtures in work-up 1. After trans-2-methyl-2-butenenitrile has been separated off, mixtures of trans-2-pentenenitrile, the 3-pentenenitriles and 4-pentenenitrile are recirculated to the 3-pentenenitrile hydrocyanation.

The reaction output from the continuous cis-2-pentenenitrile isomerization is worked up by distillation in work-up 2. cis-2-Pentenenitrile is recirculated to the isomerization, cis-2-methyl-2-butenenitrile is discharged and a mixture of trans-2-pentenenitrile and 3-pentenenitrile is recirculated to the 3-pentenenitrile hydrocyanation.

An embodiment of the continuous process of the invention for preparing adiponitrile from 3-pentenenitrile and hydrocyanic acid in the presence of nickel(0)-phosphorus ligand complexes as catalysts including the isomerization of cis-2-pentenenitrile to 3-pentenenitrile is schematically shown in FIG. 1.

The abbreviations used in FIG. 1 have the following meanings

PN: pentenenitrile
2M2BN: 2-methyl-2-butenenitrile
Isom: isomerization
Work: work-up
Hydro: hydrocyanation
R1 the reactor 1
R2 the reactor 2
Cat: catalyst
Lewis A: Lewis acid
Cat Reg: catalyst regeneration
ADN: crude adiponitrile FIG. 2 schematically shows the work-ups 1 and 2, with the meaning of the abbreviations being as indicated above.

The preferred process steps are explained in detail below. Here, the individual steps or a plurality of the steps can be applied to the four process variants according to the invention.

Process Step (a) (hydrocyanation of 3-pentenenitrile)

Process step a) comprises hydrocyanation of 3-pentenenitrile by means of hydrocyanic acid over at least one nickel (0)-phosphorus ligand complex as catalyst in the presence of free ligand and at least one Lewis acid. The hydrocyanation of 3-pentenenitrile by means of hydrocyanic acid to give adiponitrile can be carried out in a manner known per se, e.g. as described in WO 2005/073167 and in particular WO 2005/073172.

For example, the phosphorus-comprising bidentate and polydentate ligands mentioned in the present patent application, the nickel(0)-phosphorus ligand complexes prepared therewith and the Lewis acids mentioned can be used according to the invention.

Particular preference is given to bidentate and polydentate ligands from the group consisting of phosphites, phosphinites and phosphonites. Bidentate phosphites are very particularly preferred.

The use of bidentate and polydentate, phosphorus-comprising ligands in the nickel(0) catalyst complexes makes an industrially practicable isomerization of cis-2-pentenenitrile particularly advantageous.

When monodentate phosphorus ligands are used, the nickel complexes may be deactivated by the presence of 2-pentenenitriles since the amount of cis- and trans-2-pentenenitrile (based on the sum of all pentenenitriles) in the isomerization of cis-2-pentenenitrile can be above 5%, see U.S. Pat. No. 3,564,040.

Preferred Lewis acids are zinc chloride, iron chloride and triphenylborom.

The hydrocyanation output from reactor R1 (stream 1) comprises essentially the target product adiponitrile together with 2-methylglutaronitrile, unreacted 3-pentenenitrile, cis-2-pentenenitrile, trans-2-pentenenitrile, cis- and trans-2- methyl-2-butenenitrile, bidentate or polydentate nickel(0)-phosphorus ligand complexes, the associated free phosphorus-comprising ligands, degradation products thereof and at least one Lewis acid.

Process step (a) of the process of the invention is preferably carried out at an absolute pressure of from 0.1 to 10 bar, particularly preferably from 0.5 to 2 bar, in particular from 0.8 to 1.5 bar. The temperature in process step (a) is preferably from 40 to 150° C., particularly preferably from 50 to 100° C., in particular from 60 to 70° C.

Process step (a) can be carried out in any suitable apparatus known to those skilled in the art. Possible apparatuses for the reaction are apparatuses customary for this purpose, as are described, for example, in Kirk-Othmer, Encyclopedia of Chemical Technology, 4th Edition, Volume 20, John Wiley and Sons, New York 1996, pages 1040 to 1055. Examples are stirred tank reactors, loop reactors, gas circulation reactors, bubble column reactors or tube reactors, in each case optionally with devices for the removal of heat of reaction. The reaction can be carried out in a plurality of reactors, e.g. two or three reactors.

Advantageous distillation concepts for separating off the by-products cis- and trans-2-methyl-2-butenenitrile are realized according to the invention.

In the work-ups 1 and 2, two distillation apparatuses having side offtakes are used. This reduces the number of distillation apparatuses needed.

Process step (b) (work-up 1)

Part of the unreacted pentenenitriles can firstly be separated off as overhead product by distillation from the hydrocyanation output (stream 1). This preferably occurs if no phase separation is carried out in the subsequent extraction of the nickel(0) catalysts and the free ligands using hydrocarbons as extractant.

The bottom product of the partial removal of pentenenitrile comprises the at least one nickel(0) catalyst, catalyst degradation products, free ligands, the at least one Lewis acid, adiponitrile and methylglutaronitrile. The nickel(0)-phosphorus ligand complex and excess, phosphorus-comprising ligands are separated off from this mixture by extraction with hydrocarbons. The nickel(0) complexes (stream 4) are fully or partly recirculated to one of the two hydrocyanation stages or firstly entirely or partially regenerated and only then recirculated (see FIG. 1/1 in WO 2005/073172).

Particularly when using nickel(0) catalyst complexes comprising bidentate or polydentate phosphorus ligands (see, for example, US 2009/0182164A1), adiponitrile yields of over 90% are generally achieved. The amount of unreacted 3-pentenenitrile thus drops to below 10%. For this reason, a removal of pentenenitrile preceding the extraction of the catalyst is usually superfluous. This preferred variant is schematically shown in FIG. 1 (the catalyst extraction is omitted in FIG. 1).

The hydrocyanation output which has been freed of nickel(0) catalyst and phosphorus-comprising ligands is worked up by distillation, for example as described in WO 2005/073172, pages 14 to 16. It comprises essentially cis-2-methy-2-butenenitrile, cis-2-pentenenitrile, trans-2-methyl-2-butenenitrile, trans-2-pentenenitrile, cis-3-pentenenitrile, trans-3-pentenenitrile, 4-pentenenitrile, adiponitrile, methyiglutaronitrile and catalyst degradation products.

The fractional distillation of this mixture can be carried out in any suitable apparatus known to those skilled in the art. The distillation preferably takes place in at least two distillation columns. As internals for the distillation columns, preference is given to using structured sheet metal packings, structured mesh packings, bubble cap trays, dual-flow trays or beds of random packing elements and combinations thereof as separation-active internals. The distillation columns can have one or more liquid or gaseous side offtakes. Distillation columns can be configured as a dividing wall column having one or more gaseous or liquid side offtakes.

In a first distillation column having separation-active internals, a mixture of cis-2-pentenenitrile and cis-2-methyl-2-butenenitrile (stream 2) is taken off as overhead product, a mixture of trans-2-methyl-2-butenenitrile, trans-2-pentenenitrile, cis-3-pentenenitrile, trans-3-pentenenitrile and 4-pentenenitrile is taken off from a side offtake and a mixture of adiponitrile, methylglutaronitrile, Lewis acid and catalyst degradation products (stream 5) is taken off as bottom product.

The mixture of cis-2-pentenenitrile and cis-2-methyl-2-butenenitrile (stream 2) obtained as overhead product can be used as starting material for the continuous isomerization of cis-2-pentenenitrile.

However, it is also possible to separate the two compounds from one another by distillation before the isomerization, to use essentially pure cis-2-pentenenitrile for the isomerization and to discharge the cis-2-methyl-2-butenenitrile separated off, which comprises very little cis-2-pentenenitrile, from the process.

The mixture obtained from the side offtake of the first column is fractionated in a second column in such a way that trans-2-methyl-2-butenenitrile (stream 6) can be discharged as overhead product. A mixture of trans-2-pentenenitrile, cis-3-pentenenitrile, trans-3-pentenenitrile and 4-pentenenitrile (stream 3) is obtained as bottom product and is recirculated to the hydrocyanation reactor R1.

The bottom product from the first column (stream 5), which comprises adiponitrile, 2-methyl-glutaronitrile, Lewis acid and catalyst degradation products (crude adiponitrile), is worked up in further work-up steps to give pure adiponitrile suitable as fiber intermediate.

Process step c) (cis 2-pentenenitrile isomerization)

In process step c), the mixture of cis-2-pentenenitrile and cis-2-methyl-2-butenenitrile (stream 2) or essentially pure cis-2-pentenenitrile separated off in the work-up 1 is introduced into a reactor R2 and isomerized there in the presence of a heterogeneous, fixed-bed aluminum oxide catalyst to give 3-pentenenitrile-comprising pentenenitrile mixtures.

Catalysts used are aluminum oxides which can additionally comprise alkali metal and alkaline earth metal oxides or hydroxides.

Aluminum oxide can be used in different modifications or mixtures of various modifications. Preference is given to $Al_2O_3$ present in the form of beta-, gamma-, chi-, kappa-, delta-, theta- and eta-$Al_2O_3$ (M. Beller, A. Renken and R. van Santen, Catalysis, From Principles to Applications, Wiley VCH, 2012, pages 436-438). This great variety of modifications is formed on heating aluminum hydroxides to various temperatures (Römpp, Lexikon der Chemie, 10th edition 1996, keyword Aluminiumoxid, page 142). Mixed forms of the various modifications are preferentially formed here. This could be the reason for $Al_2O_3$ rarely being characterized by the particular modification on company leaflets.

Ullmanns Encyclopedia of Industrial Chemistry, 6th edition, volume 2, pages 371 to 378, Wiley VCH, 2003, page 273, 6.2 indicates that $Al_2O_3$ is used as catalyst mostly in the form of "activated $Al_2O_3$".

According to the invention, Al$_2$O$_3$ catalysts are suitable for the continuous isomerization of cis-2-pentenenitrile to 3-pentenenitrile when they have a BET surface area of from 50 to 450 m$^2$/g, preferably from 100 to 420 m$^2$/g, particularly preferably from 100 to 400 m$^2$/g. The higher the BET surface area, the faster the isomerization and the higher the space-time yield.

For the purposes of the present invention, the BET surface area is the specific surface area determined by measurement of the amount of physisorbed nitrogen gas using the method described in Brunauer, Emmett, Teller, J. am. Chem. Soc., 60, (1938), page 309.

In principle, acidic, neutral or basic aluminum oxides are suitable for the continuous isomerization of pentenenitrile mixtures comprising cis-2-pentenenitrile to 3-pentenenitrile.

The determination of the acidity, neutrality or basicity is carried out by measurement of the pH. Here, the pH values of 10% strength by weight suspensions of the respective aluminum oxide in water at room temperature (25° C.) are measured using a pH electrode.

Acidic, neutral or basic aluminum oxides having pH values of from 4 to 10.5, preferably from 7 to 10.5, can be used for the continuous isomerization according to the invention of pentenenitrile mixtures comprising cis-2-pentenenitrile to 3-pentenenitrile.

Examples of suitable catalysts are

| Al$_2$O$_3$ designation | Company | pH | BET surface area [m$^2$/g] |
|---|---|---|---|
| WA-1 Prod. No. 199966 | Sigma-Aldrich | 4.5 ± 0.5[1] acidic | 155 |
| WN-3 Prod. No. 199974 | Sigma-Aldrich | 7.0 ± 0.5[1] neutral | 155 |
| W B-2 Prod. No. 199443 | Sigma-Aldrich | 9.5 ± 0.5[1] basic | 155 |
| F-200 | BASF SE | 9.6-9.7[2] basic | 350 |
| AC 108-1000 | Nanoscale | 7.9-8.1[2] basic | 311 |
| Pural ®Mg30 MgO—Al$_2$O$_3$ | Sasol | 9.7[2] | 271 |
| 58A | Sigma-Aldrich | 6 ± 0.5 | 150 |
| WN-6 | Sigma-Aldrich | 7.3-8.0 basic | 200 |

[1]from data sheet
[2]own measurements

Thus, when using the acidic Al$_2$O$_3$ catalyst WA-1 (pH 4.5), only 10.1% of 3-pentenenitrile is obtained after a reaction time of 7 hours. On the other hand, oligomer formation is low at 0.01%.

The neutral Al$_2$O$_3$ catalyst WN-3 (pH 7) gives 22.7% of 3-pentenenitrile, viz. virtually the values of the basic catalyst F 200 (23.9%), after a reaction time of 7 hours, but isomerizes more slowly, as the 3-pentenenitrile values after 2 hours show (14.8% compared to 22.9%). The amount of oligomers increases to 0.29%.

The basic catalyst F-200 (pH 9.6-9.7) isomerizes cis-2-pentenenitrile significantly more quickly and, with 23.9%, attains the highest 3-pentenenitrile values. On the other hand, there is a large increase in the proportion of oligomers to 1.45%.

The Al$_2$O$_3$ catalysts according to the invention are preferably used as shaped bodies. For the purposes of the invention, shaped bodies are not crushed material or powder but shaped bodies which have been more or less uniformly structured by shaping processes, e.g. extrudates, pellets, cylinders, monoliths. The shaped bodies can have any three-dimensional shape.

The aluminum oxide can be present in pure form.

Here, from 10 to 100% by weight of aluminum oxides can be made up of boehmite.

In addition, it is possible to use aluminum oxide containing further compounds, e.g. rare earth metal oxides, for example cerium oxide, lanthanum oxide, praseodymium oxide, alkali metal oxides, alkaline earth metal oxides or mixtures thereof. Such compounds can be comprised in amounts of at least 10 ppm by weight and not more than 30% by weight, preferably not more than 20% by weight, in particular not more than 10% by weight, based on the sum of aluminum oxide and such compounds.

Furthermore, further anions such as hydroxyl anions can be present in addition to the oxide anion.

The total pore volume of the Al$_2$O$_3$ catalysts having a BET surface area of from 50 to 450 m$^2$/g is preferably from 0.5 to 1 cm$^3$/g, more preferably from 0.6 to 0.95 cm$^3$/g.

The space velocity over the catalyst is preferably from 0.05 to 50 kg, particularly preferably from 0.1 to 10 kg, in particular from 0.2 to 5 kg, of cis-2-pentenenitrile per liter of catalyst and hour.

The average residence time over the catalyst is preferably from 0.05 to 10 hours, particularly preferably from 0.1 to 8 hours, in particular from 0.25 to 1 hour.

The isomerization temperature is from 120 to 220° C., preferably from 150 to 220° C., more preferably from 160 to 210° C., particularly preferably from 170 to 200° C. The isomerization pressure is from 1 to 15 bar, preferably from 2 to 5 bar, more preferably from 3 to 4 bar. Preference is given to working under superatmospheric pressure in order to keep the reaction mixture liquid.

The continuous isomerization of cis-2-pentenenitrile can be carried out in the presence of a solvent which is inert under the reaction conditions. Possibilities here are, for example, hydrocarbons such as cyclohexane or n-hexane or ethers such as tetrahydrofuran or dioxane. The amount of solvent based on cis-2-pentenenitrile is from 5 to 50% by weight, preferably from 10 to 40% by weight, particularly preferably from 20 to 30% by weight. Preference is given to working in the absence of a solvent.

The continuous isomerization of cis-2-pentenenitrile can be carried out in apparatuses known to those skilled in the art.

As reactors, it is in principle possible to use all reactors which are suitable for carrying out heterogeneously catalyzed reactions in the liquid phase under superatmospheric pressure. These include reactors for the suspension mode of operation, for the fluidized-bed mode of operation and preferably for the fixed-bed mode of operation. Suitable reactors are stirred vessels, fluidized-bed reactors, jet loop reactors, jet nozzle reactors, bubble column reactors and preferably tube reactors. The isomerization can be carried out in the upflow mode or downflow mode.

In the isomerization of a mixture of cis-2-methyl-2-butenenitrile and cis-2-pentenenitrile, surprisingly only cis-2-pentenenitrile is isomerized.

It was to be expected that cis-2-methyl-2-butenenitrile will also be isomerized. In this case, 2-methyl-3-butenenitrile would be formed and would have made the work-up difficult because of its boiling point of 124° C./1013 mbar. This does not occur. Cis-2-methyl-2-butenenitrile is partly isomerized to trans-2-methyl-2-butenenitrile, which is recycled via stream 10 in reactor (R1) and exits after work-up 1 (FIGS. 1 and 2).

It is also known that acrylonitrile polymerizes easily (Beyer/Walter, Lehrbuch der Organischen Chemie, 24th edition, page 254, S. Hirzel Verlag Stuttgart/Leipzig).

cis- and trans-2-pentenenitrile are isomeric 3-ethylacrylonitriles. The experiments on the isomerization of cis-2-pentenenitrile carried out continuously at from 126 to 144° C. in the presence of aluminum oxides as catalyst show that oligomers (dimers) are formed (see the following examples). Here, the amount of oligomers increases with increasing BET surface area and increasing basicity of the aluminum oxides.

It was not possible to foresee whether significantly greater oligomer formation would take place in the isomerization according to the invention at preferably from 150 to 220° C. Rapid deactivation of the catalyst as a result of it being coated with oligomers, blockage of the isomerization apparatus and/or a significant loss of pentenenitriles could be the consequence.

Surprisingly, a long catalyst operating life of over 3000 hours and a tolerable level of oligomer formation was observed in the continuous experiment.

Process step (d) (work-up 2, see FIG. 1 and FIG. 2)

The reaction output from the continuous isomerization of cis-2-pentenenitrile (stream 7) comprises essentially unreacted cis-2-pentenenitrile, trans-2-pentenenitrile, cis-3-pentenenitrile, trans-3-pentenenitrile, 4-pentenenitrile and, if not already separated off in work-up 1, also cis-2-methyl-2-butenenitrile.

If cis-2-methyl-2-butenenitrile is still comprised in stream 7, it is separated off as overhead product from cis-2-pentenenitrile in a distillation apparatus (stream 8) and discharged.

Any unreacted cis-2-pentenenitrile is taken off from a side offtake and recirculated to the continuous isomerization R2 (stream 9).

The bottom product from the distillation apparatus (stream 10) comprises essentially trans-2-pentenenitrile, cis-3-pentenenitrile, trans-3-pentenenitrile and 4-pentenenitrile.

Stream 3 is, like stream 10, recirculated to the 3-pentenenitrile hydrocyanation. Here, the two streams can be recirculated individually or after having been combined.

Alternative process step c) (reactive distillation of cis-2-pentenenitrile)

In a preferred process step c), the continuous isomerization of cis-2-pentenenitrile to 3-pentenenitrile (process step c)) is carried out in the form of a reactive distillation. A reactive distillation can combine the above steps c) and d). Reactive distillation of cis-2-pentenenitrile to give 3-pentenenitrile means that the continuous isomerization of cis-2-pentenenitrile to 3-pentenenitrile and the work-up of the isomerization output by distillation is combined in an apparatus in which the isomerization and the work-up of the isomerization mixture by distillation take place. In FIG. 1, the isomerization reactor R2 and the work-up 2 are then combined to form one catalyst-comprising apparatus from which, when the conversion of cis-2-pentenenitrile is complete and 2-methyl-2-butenenitrile has been separated off beforehand, a stream which is composed of trans-2-pentenenitrile, cis- and trans-3-pentenenitrile and 4-pentenenitrile and can be recycled to the 3-pentenenitrile hydrocyanation can be taken off.

The isomerization of cis-2-pentenenitrile to 3-pentenenitrile in the presence of aluminum oxide as catalyst is described as a reactive distillation in WO 20051073177A1. The apparatus described there can be employed.

The reaction conditions of the continuous cis-2-pentenenitrile isomerization, e.g. temperature, pressure, residence time and materials properties such as BET surface area, pore volume and pH values of the $Al_2O_3$, described in the present application apply for the reactive distillation according to the invention.

The invention is illustrated by the following examples.

EXAMPLES

Batchwise Isomerization of cis-2-pentenenitrile (Orienting Experiments, Not According to the Invention)

The batchwise isomerization of cis-2-pentenenitrile was carried out in a 250 ml multineck flask provided with stirrer, thermometer, condenser and septum for sampling. In each experiment, 120 g of cis-2-pentenenitrile from Merck (CAS 25899-50-7) were initially placed in the flask.

The cis-2-pentenenitrile was admixed with 10% by weight of $Al_2O_3$ powder (triturated to powder in a mortar) as per the following table and heated under reflux (from 126 to 144° C.) at atmospheric pressure for 7 hours. During the course of the isomerization, the temperature increased as a result of the formation of pentenenitriles having boiling points higher than that of cis-2-pentenenitrile.

After 15 and 30 minutes, then after one hour in each case, samples were taken and analyzed by gas chromatography to determine their content of pentenenitriles.

A CP-Wax52CB separation column was used as GC column. The GC temperature program was 5 minutes isothermal at 50° C., then 8° C. temperature increase per minute up to a final temperature of 240° C.

The pH values for the aluminum oxides are either taken from the product data sheets of the manufacturers or were measured.

For pH measurements in the laboratory, 5 g of catalyst powder were placed together with 45 g of water in a glass beaker and the resulting 10% strength by weight suspension was stirred at room temperature by means of a stirrer (5000 revolutions per minute). The pH was measured at various times (e.g. after 5 and 30 minutes) by means of a calibrated pH electrode (Blue Line 18 pH, SI. Analysis) until a constant value was obtained.

The table shows batchwise isomerization results in the presence of aluminum oxides as catalysts as a function of increasing BET surface area and increasing pH. The results show that the rate of isomerization increases with increasing BET surface area and increasing pH. However, increasing amounts of oligomers (including dimers) were observed at the same time.

| Example No. | $Al_2O_3$ type | Company | pH | BET surface area [m$^2$/g] | Reaction time [h] | c-2 PN | t-2 PN | c- + t - 3 PN + 4 PN | Oligomers |
|---|---|---|---|---|---|---|---|---|---|
| C1 | alpha-$Al_2O_3$ | NorPro | 8.4-8.7[2)] | 1 | 2 7 | 99.1 | 0 | 0.4 | 0 |
| 2 | 58A | Sigma-Aldrich | 6 ± 0.5 acidic | 150 | 7 | 59.5 | 19.6 | 19.8 | 0.13 |

-continued

| Example No. | Al$_2$O$_3$ type | Company | pH | BET surface area [m$^2$/g] | Reaction time [h] | c-2 PN | t-2 PN | c- + t - 3 PN + 4 PN | Oligomers |
|---|---|---|---|---|---|---|---|---|---|
| 3 | WN-3 Prod. No. 199974 | Sigma-Aldrich | 7.0 ± 0.5[1] Neutral | 155 | 7 | 46.5 | 29.6 | 22.7 | 0.29 |
| 4 | W B-2 Prod. No. 199443 | Sigma-Aldrich | 9.5 ± 0.5[1] Basic | 155 | 7 | 40.8 | 34.8 | 23.2 | 0.35 |
| 5 | WN-6 | Sigma-Aldrich | 7.3-8.0 Basic | 200 | 7 | 42.9 | 32.5 | 23.4 | 0.31 |
| 6 | F-200 | BASF SE | 9.6-9.7[2] Basic | 350 | 7 | 39.6 | 34.2 | 23.9 | 1.45 |
| 7 | AC 108-1000 | Nanoscale | 7.9-8.1[2] Basic | 311 | 2 | 33.6 | 38.1 | 23.6 | 3.7 |
|  |  |  |  |  | 7 | 32.2 | 38.0 | 23.2 | 5.7 |
| 8 | Pural Mg 30 MgO-Al$_2$O$_3$ | Sasol | 9.7 Basic | 271 | 2 | 37.7 | 30.5 | 23.4 | 7.6 |
|  |  |  |  |  | 7 | 34.3 | 33.5 | 22.8 | 8.5 |

[1]from data sheet
[2]own measurements

It was determined by GC-MS coupling that the high boilers in the retention time range from 22.5 to 28 minutes are pentenenitrile dimers having a molecular weight of 162.

The oligomer content of the reaction outputs is reported in percent by area: (sum of the dimer areas divided by the sum of all areas)×100.

The qualitative composition of aluminum oxides was determined by XRD analysis:

The aluminum oxides 58A, WA-1, WN-3, WN-6 and WB-2 have the same XRD spectra. The crystallinity is low. gamma-Al$_2$O$_3$ (tetragonal) and chi-Al$_2$O$_3$ (cubic) were found as phases.

The Al$_2$O$_3$ catalyst F-200 likewise has a low crystallinity. Boehmite AlO (OH) (orthorhombic) was comprised as main phase, additionally as in the case of the preceding catalysts gamma-Al$_2$O$_3$ (tetragonal) and chi-Al$_2$O$_3$ (cubic).

Continuous isomerization of cis-2-pentenenitrile (operating life experiment)

The continuous isomerization of cis-2-pentenenitrile to give pentenenitrile isomer mixtures comprising 3-pentenenitrile was carried out in the presence of Al$_2$O$_3$ balls (3.2 mm diameter) of the type Alcoa F-200, which had a BET surface area of 350 m$^2$/g, a pH of from 9.6 to 9.7 and a total pore volume of 0.59 ml/g.

The cis-2-pentenenitrile used had a purity of 98.8%, with the balance to 100% consisting of other unsaturated isomeric C5-nitriles.

The isomerization was carried out in the upflow mode in a 250 ml tube reactor (reactor geometry 25 mm×450 mm). 130.6 g of Al$_2$O$_3$ catalyst were placed in the reactor. This corresponds to 250 ml of catalyst. The reactor was then pressurized with 7 bar of argon and the pressure regulator was set to 10 bar.

Commencing at an isomerization temperature of 125° C. and a pressure of 10 bar, 31.2 ml/h (25 g/h) of cis-2-pentenenitrile (space velocity over the catalyst 0.1 kg of cis-2-pentenenitrile per liter of catalyst and hour=100 kg of cis-2-pentenenitrile per m$^3$ of catalyst and hour) were fed into the reactor.

FIG. 3 shows that, at a constant space velocity over the catalyst, the temperature firstly increases to 200° C. (autogenous pressure at 200° C. about 4 bar) over a period of 1000 hours and the reaction was carried out under the same reaction conditions for a further 1800 hours.

After 2800 hours, the space velocity over the catalyst was increased to 0.2 kg of cis-2-pentenenitrile per liter of catalyst and hour, which led to a changed curve. The experiment was stopped after a total of 3200 hours. The Al$_2$O$_3$ catalyst could be removed from the reactor without problems.

FIG. 3 shows the amounts (Content in percent by area in the gas chromatogram) of cis- and trans-3-pentenenitrile (PN) formed as a function of temperature (T) and reaction time (L), The graph shows that no deactivation of the catalyst was observed over the entire period of 3200 hours. Blockages caused by high boilers (oligomers) did not occur.

Table 3 shows that amounts of cis-+trans-3-pentenenitrile of from 19.2 to 23.9% were achieved within from 1000 to 2800 hours reaction time; values of from 21.9 to 19.3% were achieved at higher space velocity within from 2800 to 3200 hours.

Amounts of oligomers in the range from 0.3 to 2.0% were measured by gas chromatography.

Since it is possible that not all oligomers are measurable by gas chromatography, 100 g of the isomerization output were in each case distilled at 120° C. and 5 mbar via a distillation bridge. The distillate receiver was cooled. The amount of nonvolatile residue was on average from 1.0 to 1.5 g per 100 g of isomerization output, and the amounts of distillate were in the range from 98.5 to 99 g. The amounts of oligomers determined by gas chromatography were thus confirmed.

TABLE 3

Continuous isomerization of cis-2-pentenenitrile

| Reaction time [h] | c-2PN | t-2PN | c- + t-3PN + 4-PN | Oligomers | Total % by area |
|---|---|---|---|---|---|
|  |  | GC-% by area |  |  |  |
| 501 | 69.6 | 13.4 | 15.8 |  | 98.8 |
| 1006 | 50.5 | 25.7 | 21.2 |  | 97.4 |
| 1506 | 56.8 | 20.2 | 19.2 | 0.3 | 96.5 |
| 2011 | 43.8 | 29.2 | 23.4 | 1.0 | 97.4 |
| 2490 | 39.6 | 31.0 | 23.9 | 2.0 | 96.5 |
| 3017 | 50.3 | 26.0 | 21.9 | 0.7 | 98.9 |
| 3196 | 61.0 | 17.0 | 19.3 |  | 97.3 |

The invention claimed is:

1. A process for the continuous preparation of adiponitrile by hydrocyanation of 3-pentenenitrile, wherein
   a) 3-pentenenitrile or a mixture comprising 3-pentenenitrile is hydrocyanated by means of hydrocyanic acid in the presence of at least one nickel(0) complex as catalyst, free ligand, and at least one Lewis acid in a reactor R1 to give a reaction output comprising adiponitrile, 2-methylglutaronitrile, the nickel(0) complex, free ligand, Lewis acid, catalyst degradation products, unreacted 3-pentenenitrile and, as secondary components, cis- and trans-2-methyl-2-butenenitrile and also cis- and trans-2-pentenenitrile, b) in a work-up 1, a mixture comprising cis-2-methyl-2-butenenitrile and cis-2-pentenenitrile is separated off as overhead product, a mixture comprising adiponitrile, nickel(0) complex, free ligand, at least one Lewis acid and catalyst degradation products is separated off as bottom product and a mixture comprising trans-2-methyl-2-butenenitrile, trans-2-pentenenitrile and 3-pentenenitrile is separated off at a side offtake from the reaction output from the reactor R1 in a first distillation apparatus, and the side offtake product is fractionated in a second distillation apparatus in such a way that trans-2-methyl-2-butenenitrile is separated off as overhead product and discharged and 3-pentenenitrile and trans-2-pentenenitrile are obtained as bottom product and recirculated to the 3-pentenenitrile hydrocyanation in step a), c) the mixture comprising cis-2-methyl-2-butenenitrile and cis-2-pentenenitrile from step b) is continuously isomerized in the presence of aluminum oxide as catalyst in a reaction zone in a reactive distillation column R2 to give a 3-pentenenitrile-comprising product mixture, where the isomerization is carried out at temperatures of from 150 to 220° C. and pressures of from 1 to 15 bar in the liquid phase and the aluminum oxide has a BET surface area of from 50 to 450 m$^2$/g and a pH of from 7 to 10.5, and cis-2-methyl-2-butenenitrile is separated off as overhead product and discharged, unreacted cis-2-pentenenitrile is separated off from a side offtake and recirculated to the reactor R2 in step c) and the 3-pentenenitrile-comprising bottom product is recirculated to the 3-pentenenitrile hydrocyanation in step a).

2. A process for the continuous preparation of adiponitrile by hydrocyanation of 3-pentenenitrile, wherein a) 3-pentenenitrile or a mixture comprising 3-pentenenitrile is hydrocyanated by means of hydrocyanic acid in the presence of at least one nickel(0) complex as catalyst, free ligand, and at least one Lewis acid in a reactor R1 to give a reaction output comprising adiponitrile, 2- methylglutaronitrile, the nickel(0) complex, free ligand, Lewis acid, catalyst degradation products, unreacted 3-pentenenitrile and, as secondary components, cis- and trans-2-methyl-2-butenenitrile and also cis- and trans-2-pentenenitrile, b) in a work-up 1, only cis-2-methyl-2-butenenitrile is separated off as overhead product and all remaining compounds are separated off as bottom product from the reaction output from the reactor R1 in a first distillation apparatus and the bottom product from the first distillation apparatus is fractionated in a second distillation apparatus in such a way that cis-2-pentenenitrile is obtained as overhead product, 3-pentenenitrile, trans-2-pentenenitrile and trans-2-methyl-2-butenenitrile are obtained via a side offtake and crude adiponitrile, nickel(0) complex, free ligand, the at least one Lewis acid and catalyst degradation products are obtained as bottom product and the side offtake product from the second distillation apparatus is distilled in a third distillation apparatus in such a way that trans-2-methyl-2-butenenitrile is discharged as overhead product and a mixture comprising trans-2-pentenenitrile and 3-pentenenitrile is separated off as bottom product and recirculated to the 3-pentenenitrile hydrocyanation in step a), c) cis-2-pentenenitrile from step b) is continuously isomerized in the presence of aluminum oxide as catalyst in a reaction zone in a reactive distillation column R2 to give a 3-pentenenitrile-comprising product mixture, where the isomerization is carried out at temperatures of from 150 to 220° C. and pressures of from 1 to 15 bar in the liquid phase and the aluminum oxide has a BET surface area of from 50 to 450 m$^2$/g and a pH of from 7 to 10.5, and unreacted cis-2-pentenenitrile is separated off as overhead product and recirculated to the reactor R2 in step c) and the 3-pentenenitrile-comprising bottom product is recirculated to the 3-pentenenitrile hydrocyanation in step a).

3. The process according to claim 1, wherein beta-, gamma-, chi-, kappa-, delta-, theta-, eta-aluminum oxide or mixtures of these aluminum oxides are used as catalyst as aluminum oxide in step c).

4. The process according to claim 1 wherein from 10 to 100% by weight of the aluminum oxides is made up of boehmite in step c).

5. The process according to claim 1 wherein the aluminum oxide is used as shaped bodies in step c).

6. The process according to claim 1, wherein the aluminum oxide in step c) comprises from 10 ppm by weight to 30% by weight of further compounds, based on the sum of aluminum oxide and such compounds.

7. The process according to claim 1 wherein the BET surface area of the aluminum oxide in step c) is from 100 to 420 m$^2$/g.

8. The process according to claim 1, wherein the space velocity over the catalyst in step c) is from 0.05 to 50 kg of cis-2-pentenenitrile per liter of aluminum oxide per hour.

9. The process according to claim 1, wherein the cis-2-pentenenitrile isomerization in step c) is carried out in the upflow or downflow mode in a tube reactor.

10. The process according to claim 1, wherein the catalyst in step a) comprises bidentate or polydentate phosphites, phosphinites, phosphonites and/or phosphines as ligands.

11. The process according to claim 1, wherein the 3-pentenenitrile used in the process originates from the hydrocyanation of butadiene.

12. The process according to claim 2, wherein beta-, gamma-, chi-, kappa-, delta-, theta-, eta-aluminum oxide or mixtures of these aluminum oxides are used as catalyst as aluminum oxide in step c).

13. The process according to claim 2, wherein from 10 to 100% by weight of the aluminum oxides is made up of boehmite in step c).

14. The process according to claim 2, wherein the aluminum oxide is used as shaped bodies in step c).

15. The process according to claim 2, wherein the aluminum oxide in step c) comprises from 10 ppm by weight to 30% by weight of further compounds, based on the sum of aluminum oxide and such compounds.

16. The process according to claim 2, wherein the BET surface area of the aluminum oxide in step c) is from 100 to 420 m$^2$/g.

17. The process according to claim wherein the space velocity over the catalyst in step c) is from 0.05 to 50 kg of cis-2-pentenenitrile per liter of aluminum oxide per hour.

18. The process according to claim 2, wherein the cis-2-pentenenitrile isomerization in step c) is carried out in the upflow or downflow mode in a tube reactor.

19. The process according to claim 2, wherein the catalyst in step a) comprises bidentate or polydentate phosphites, phosphinites, phosphonites and/or phosphines as ligands.

20. The process according to claim 2, wherein the 3-pentenenitrile used in the process originates from the hydrocyanation of butadiene.

* * * * *